United States Patent
Lewin et al.

(10) Patent No.: US 10,882,241 B2
(45) Date of Patent: Jan. 5, 2021

(54) METHOD AND DEVICE FOR BLOW-MOLDING CONTAINERS WHICH ARE STERILE AT LEAST IN SOME AREAS

(71) Applicant: KHS Corpoplast GmbH, Hamburg (DE)

(72) Inventors: Frank Lewin, Tangstedt (DE); Thomas Herold, Ahrensburg (DE); Jan Fabian Meyer, Hamburg (DE); Martin Gerhards, Hamburg (DE); Dieter Klatt, Hamburg (DE); Rolf Baumgarte, Ahrensburg (DE)

(73) Assignee: KHS CORPOPLAST GMBH, Hamburg (DE)

( * ) Notice: Subject to any disclaimer, the term of this patent is extended or adjusted under 35 U.S.C. 154(b) by 739 days.

(21) Appl. No.: 14/911,676

(22) PCT Filed: Aug. 13, 2014

(86) PCT No.: PCT/EP2014/002221
§ 371 (c)(1),
(2) Date: Feb. 11, 2016

(87) PCT Pub. No.: WO2015/024642
PCT Pub. Date: Feb. 26, 2015

(65) Prior Publication Data
US 2016/0200028 A1 Jul. 14, 2016

(30) Foreign Application Priority Data
Aug. 19, 2013 (DE) .................. 10 2013 013 591

(51) Int. Cl.
*B29C 49/46* (2006.01)
*B29C 49/42* (2006.01)
(Continued)

(52) U.S. Cl.
CPC ...... *B29C 49/4252* (2013.01); *B29C 49/0031* (2013.01); *B29C 49/063* (2013.01);
(Continued)

(58) Field of Classification Search
CPC ..... B29C 49/4252; B29C 49/12; B29C 49/58; B29C 49/4268; B29C 49/28; B29C 49/46;
(Continued)

(56) References Cited

U.S. PATENT DOCUMENTS

| | | |
|---|---|---|
| 4,076,071 A | 2/1978 | Rosenkranz et al. |
| 5,346,386 A | 9/1994 | Albrecht et al. |

(Continued)

FOREIGN PATENT DOCUMENTS

| | | |
|---|---|---|
| CN | 101992541 A | 3/2011 |
| DE | 1171299 B | 5/1964 |

(Continued)

OTHER PUBLICATIONS

Heraeus (https://www.heraeus.com/en/hqs/fused_silica_quartz_knowledge_base/properties/properties.aspx).*

(Continued)

Primary Examiner — Xiao S Zhao
Assistant Examiner — Ninh V Le
(74) Attorney, Agent, or Firm — Lucas & Mercanti, LLP; Klaus P. Stoffel

(57) ABSTRACT

A method and a device for producing blow-molded containers, which are sterile at least in some areas, in a blow-molding machine. A preform made of a thermoplastic material is first heated, then stretched by a stretching rod in a blowing station, and then supplied with a pressurized fluid via a blow nozzle, wherein a sterilization device is arranged in the blowing station. The sterilization device has at least (Continued)

one radiation source which emits a sterilizing radiation onto the stretching rod and/or onto the blow nozzle.

12 Claims, 6 Drawing Sheets

(51) Int. Cl.
<table>
<tr><td>B29C 49/28</td><td>(2006.01)</td></tr>
<tr><td>B29C 49/64</td><td>(2006.01)</td></tr>
<tr><td>B29C 49/12</td><td>(2006.01)</td></tr>
<tr><td>B29C 49/58</td><td>(2006.01)</td></tr>
<tr><td>B29C 49/00</td><td>(2006.01)</td></tr>
<tr><td>B29C 49/06</td><td>(2006.01)</td></tr>
<tr><td>B29K 67/00</td><td>(2006.01)</td></tr>
<tr><td>B29K 105/00</td><td>(2006.01)</td></tr>
<tr><td>B29L 31/00</td><td>(2006.01)</td></tr>
<tr><td>B29C 49/36</td><td>(2006.01)</td></tr>
<tr><td>A61L 2/00</td><td>(2006.01)</td></tr>
</table>

(52) U.S. Cl.
CPC ............. *B29C 49/12* (2013.01); *B29C 49/28* (2013.01); *B29C 49/4268* (2013.01); *B29C 49/46* (2013.01); *B29C 49/58* (2013.01); *B29C 49/6409* (2013.01); *A61L 2/00* (2013.01); *A61L 2202/23* (2013.01); *B29C 49/06* (2013.01); *B29C 49/36* (2013.01); *B29C 2049/1228* (2013.01); *B29C 2049/4635* (2013.01); *B29C 2049/4679* (2013.01); *B29C 2049/5886* (2013.01); *B29K 2067/003* (2013.01); *B29K 2105/258* (2013.01); *B29L 2031/712* (2013.01)

(58) Field of Classification Search
CPC ..... B29C 49/6409; B29C 49/06; B29C 49/36; B29C 49/063; B29C 49/421; B29C 49/0031; B29C 2049/4679; B29C 2049/4682; B29C 2049/1228; B29C 2049/4694; B29C 2049/4635; B29C 2049/5886; A61L 2/00; A61L 2/26; A61L 2202/23; B67C 7/004; B67C 7/0073; B67C 7/0086; B08B 9/30
See application file for complete search history.

(56) References Cited

U.S. PATENT DOCUMENTS

| | | | |
|---|---|---|---|
| 5,648,026 A | 7/1997 | Weiss | |
| 6,692,684 B1 | 2/2004 | Nantin et al. | |
| 8,708,680 B2 | 4/2014 | Geltinger et al. | |
| 8,985,991 B2 | 3/2015 | Winzinger et al. | |
| 9,079,345 B2 | 7/2015 | Chauvin et al. | |
| 9,144,932 B2 | 9/2015 | Pagliarini et al. | |
| 2002/0171179 A1* | 11/2002 | Dundas | A61F 2/28 264/401 |
| 2010/0047120 A1 | 2/2010 | Adriansens et al. | |
| 2010/0089009 A1 | 4/2010 | Till | |
| 2011/0031167 A1 | 2/2011 | Augst | |
| 2011/0037187 A1* | 2/2011 | Winzinger | B08B 9/00 264/39 |
| 2011/0061690 A1 | 3/2011 | Seger | |
| 2011/0133370 A1 | 6/2011 | Engelhard et al. | |
| 2011/0311675 A1* | 12/2011 | Voth | B29C 49/42 425/526 |
| 2012/0091636 A1* | 4/2012 | Voth | B29C 49/4205 264/535 |
| 2013/0069285 A1 | 3/2013 | Pagliarini et al. | |

FOREIGN PATENT DOCUMENTS

| | | | | |
|---|---|---|---|---|
| DE | 2352926 | A1 | 4/1975 | |
| DE | 4212583 | A1 | 10/1993 | |
| DE | 4340291 | A1 | 6/1995 | |
| DE | 19906438 | A1 | 8/2000 | |
| DE | 102007017938 | A1 | 10/2008 | |
| DE | 102009015088 | A1 | 10/2010 | |
| EP | 1258336 | A1 | 11/2002 | |
| EP | 1086019 | B1 | 9/2005 | |
| EP | 1896245 | A1 | 3/2008 | |
| EP | 2138298 | A2 * | 12/2009 | ............ A61L 2/087 |
| EP | 2283991 | A2 | 2/2011 | |
| EP | 2295223 | A2 | 3/2011 | |
| EP | 2388127 | A2 | 11/2011 | |
| EP | 2483052 | A2 | 8/2012 | |
| JP | H04147824 | A | 5/1992 | |
| JP | 2011527246 | A | 10/2011 | |
| WO | 2010003873 | A1 | 1/2010 | |
| WO | 2010020530 | A1 | 2/2010 | |
| WO | 2011154868 | A2 | 12/2011 | |
| WO | WO2011154868 | A2 * | 12/2011 | |
| WO | 2013093634 | A2 | 6/2013 | |

OTHER PUBLICATIONS

Accuratus (http://web.archive.org/web/20021102113755/http://accuratus.com/fused.html).*

Physlink (http://web.archive.org/web/20020124161828/http://www.physlink.com/education/askexperts/ae47.cfm).*

\* cited by examiner

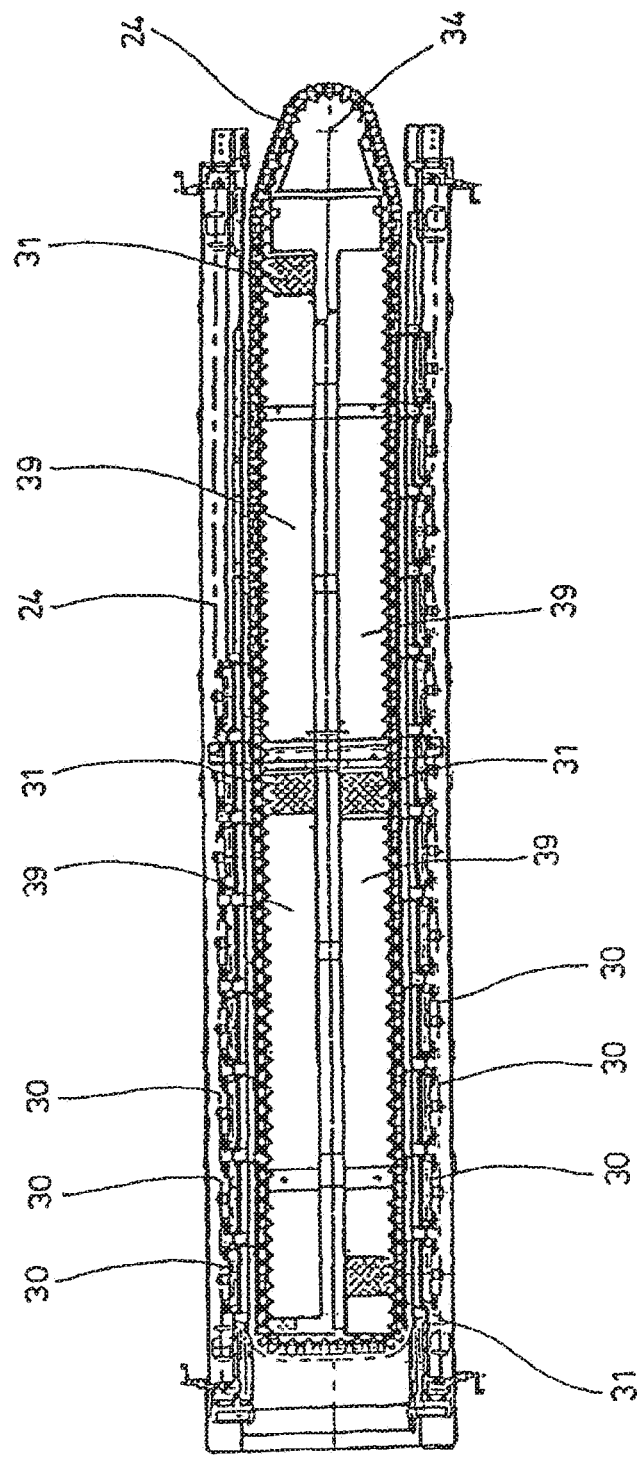

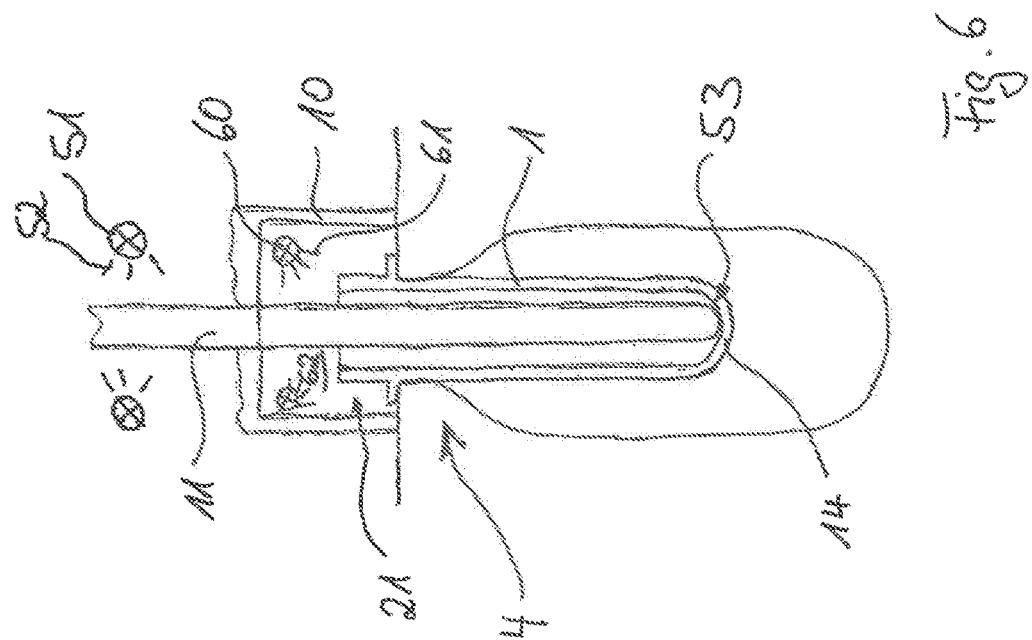
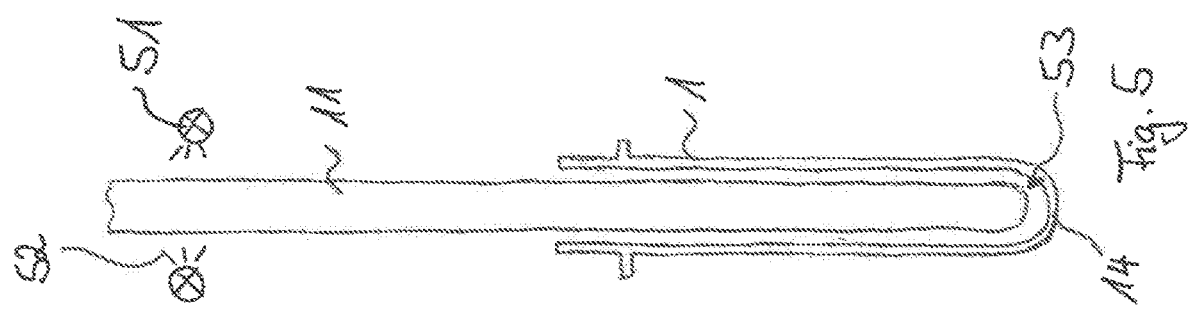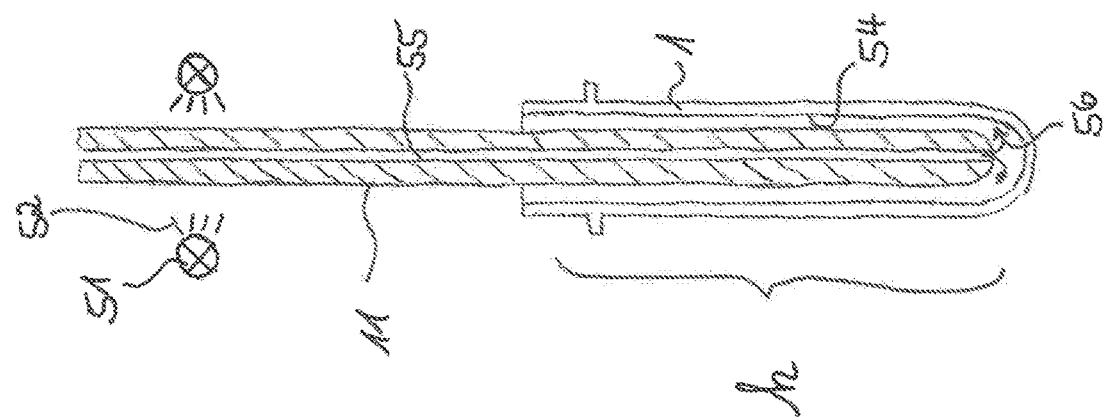

METHOD AND DEVICE FOR BLOW-MOLDING CONTAINERS WHICH ARE STERILE AT LEAST IN SOME AREAS

The present application is a 371 of International application PCT/EP2014/002221, filed Aug. 13, 2014, which claims priority of DE 10 2013 013 591.5, filed Aug. 19, 2013, the priority of these applications is hereby claimed and these applications are incorporated herein by reference.

BACKGROUND OF THE INVENTION

The invention relates to a method for manufacturing blow-molded containers which are sterile in at least some areas, in which method a preform made from a thermoplastic material is initially heated and then stretched by a stretching rod in a blowing station and by way of a blowing nozzle is impinged with a pressurized fluid, and in which method a sterilization installation is disposed in the blowing station.

Moreover, the invention relates to a device for manufacturing blow-molded containers which are sterile in at least some areas, which device is provided with a heating section for temperature controlling preforms and with a blowing station for blow-molding the preforms to form containers, wherein the blowing station has stretching rod, and in which device a sterilization installation is disposed in the blowing station.

Manufacturing of sterile blow-molded containers is typically performed in that these containers after blow-molding thereof and prior to filling are sterilized using hydrogen peroxide or other chemicals. It is likewise already known for the preforms, in particular the area of the internal surface of these preforms, which in blow-molding of the containers are used as the primary product, to be sterilized.

In the case of container molding by way of the effect of blowing pressure, preforms from a thermoplastic material, for example preforms from PET (polyethylene terephthalate) within a blowing machine are supplied to various processing stations. A blowing machine of this type typically has a heating installation and a blowing station, in the area of which the preform, which prior thereto has been temperature controlled, is expanded by way of biaxial orientation to form a container. Expansion is performed with the aid of compressed air which is directed into the preform to be expanded by means of a blowing nozzle. The process-technological sequence of expanding the preform in such a manner is set forth in DE-OS 43 40 291.

The in-principle construction of a blowing station for molding containers is described in DE-OS 42 12 583. Possibilities for temperature controlling the preforms are set forth in DE-OS 23 52 926.

Within the device for blow molding, the preforms and the blown containers may be conveyed with the aid of various handling installations. The use of conveying mandrels onto which the preforms may be push-fitted has proven particularly successful. However, the preforms may also be handled using other carrying installations. The use of gripping tongs for handling preforms, and the use of expanding mandrels which for mounting are introducible into a mouth area of the preform, inter alia are likewise available constructions.

Handling containers using transfer wheels in an arrangement of the transfer wheel between a blowing wheel and a deliver section is described in DE-OS 199 06 438, for example.

Handling of the preforms as has already been set forth is performed, on the one hand, in the so-called dual-stage methods in which the preforms are initially manufactured in an injection-molding method, are thereafter temporarily stored and are only later conditioned in terms of their temperature and blown to form a container. On the other hand, an application is performed in the so-called single-stage methods in which the preforms are suitably temperature controlled and subsequently blown immediately after having been manufactured by injection-molding technology and having sufficiently solidified.

In terms of the blowing stations used, various embodiments are known. In the case of blowing stations which are disposed on rotating conveying wheels, book-like unfolding capability of the mold carriers may often be encountered. However, it is also possible for mold carriers which are mutually displaceable or embodied in another manner to be employed. In the case of locationally fixed blowing stations which are in particular suitable for receiving a plurality of cavities for container molding, plates which are disposed so as to be mutually parallel are typically used as mold carriers.

In terms of sterilizing preforms, various methods and devices which, however, all have method-specific disadvantages, are already known from the prior art, said disadvantages impeding reliable sterilization of the preforms at simultaneously high output rates.

Sterilizing hot preforms using a hot gaseous sterilization means is described in EP-A 1 086 019, for example. Separate treatment stations which are sequentially disposed are used, namely a first heating module, a sterilizing module, and a second heating module. Here, the temperature-related behavior of the preform during the sterilizing procedure and uncontrolled leakage of the sterilization means from the preform within the heating unit are disadvantageous.

A method in which a gaseous sterilization means is directed into a cold preform and condensates therein prior to heating is described in EP-A 1 896 245. Ensuring overall formation of condensate on the entire internal face of the preform is problematic here, since the hot sterilization means streaming in increases the internal wall temperature of the preform. Moreover, here too the sterilization means after evaporation thereof in the area of the heating unit within the heating unit leaks in an uncontrolled manner from the preform.

A device in which sterilizing installations are disposed in a precautionary manner both in front of the blowing module used and behind the blowing module used is described in EP-A 2 138 298. This results in great complexity in terms of the construction of the machine.

The arrangement of a sterilizing installation between a heating unit and the blowing module is described in WO 2010/020530 A1. In this method, the amount of sterilization means to be applied into the area of the blowing module is foreseeable only with great difficulty. Moreover, the amount of sterilization means being released into the environment is uncontrollable and corresponding contamination is not excluded.

Once sterilizing and heating of the preforms has been performed, the latter are supplied to a blowing station and, using sterile blowing air, there are formed into the containers. The supply of blowing air and infeeding of the blowing air is performed by means of a blowing nozzle which bears in a sealing manner on the preform, for example. During blow-forming of the containers the used blowing air streams out of the stretching rod or past the stretching rod, for example. Moreover, the stretching rod in the area of the stretching rod dome comes into contact with both the preform as well as the blown container. In order for sufficient sterility of the blown containers to be guaranteed, it is thus necessary that sufficient sterility of the stretching rod is also provided for. The blowing nozzle should also be kept sterile, so as to be avoid germ infestation of the preforms. A method which is reliable and at the same time implementable in a technically simple manner is not known to date.

SUMMARY OF THE INVENTION

It is an object of the present invention to improve a method of the type mentioned at the outset in such a manner that sufficient sterility may be guaranteed in a simple manner.

This object is achieved according to the invention in that a sterilization installation which has at least one radiation source and which emits a sterilizing radiation onto the stretching rod and/or onto the blowing nozzle is disposed in the blowing station.

It is a further object of the invention to construct a device of the type mentioned at the outset in such a manner that effective sterility is guaranteed at low complexity.

This object is achieved according to the invention in that a sterilization installation which has at least one radiation source and which emits a sterilizing radiation onto the stretching rod and/or onto the blowing nozzle is disposed in the blowing station.

On account of the stretching rod and/or the blowing nozzle being sterilized in the area of the blowing station, it is possible for labor-intensive installation and removal procedures which would be required for external sterilizing of the stretching rod or of the blowing nozzle to be avoided. The use of sterilizing radiation in the blowing station has the further advantage that non-contacting radiation of the areas to be sterilized, in particular in a manner not interfering with the blowing process, is possible. It is merely required that radiation sources are disposed at suitable positions in the blowing station, to align the former with the areas to be sterilized, and to connect the former to supply lines. A further advantage of the present invention is that the emitters may permanently emit the sterilizing radiation, this to be understood to mean also pulsating emission of radiation. This is an eminent advantage specifically in keeping the stretching rod, the blowing nozzle, or the preform sterile, since the emitters may be switched on during the entire running time of the blowing machine, for example.

For sterile keeping it is advantageous that the emitters may also remain in operation even during a temporary interruption of the blowing process. Such interruptions during which the blowing machine is not shut down are referred to as an inline operation. During this inline operation the emitters may continue to deploy the germ-killing and sterile keeping effect. In order for the stretching rod and the blowing nozzle to be sterilized during start-up of the blowing machine, it is advantageous that the emitters are also in operation during this period of time and emit sterilizing radiation. Sterile keeping means preventing renewed germ infestation of an area which has already been sterilized, while sterilizing means removal of germs which are present.

Various emitters may be considered as radiation sources. However, UV emitters which in comparison with alternative radiation sources such as, for example, electron emitters, microwave emitters, or x-ray emitters are distinguished in that they are simpler in terms of technical handling and that less complexity arises in their shielding are preferred radiation sources. Suitable UV emitters are known in the prior art, for example UV LEDs, low-pressure amalgam lamps, mercury vapor lamps (low pressure, medium pressure, high pressure and maximum pressure), excimer lasers, and diode lasers.

Preferably, UV emitters which emit radiation which in particular is in a wavelength range which is suitable for sterilizing, for example in a range from 180 to 300 nm, either in a narrow band or in a wide band, either pulsated or in a continuously emitting operation, are disposed as radiation sources. It is seen as being optimal for the radiation to be intense in the range of 220 nm and/or 265 nm.

It is advantageously proposed that the stretching rod is configured from a UV radiation conducting material, in particular from a quartz glass, and UV radiation is irradiated into the stretching rod, directed from the stretching rod into the preform and emitted onto the internal wall of the preform. On account thereof, not only is the stretching rod sterilized or kept sterile, respectively, but also the internal wall of the preform of the preform. Suitable types of glass are known in the prior art, for example from DE 10 2009 015 088 A1.

This is further advantageously supported in that the stretching rod has at least one internal duct, and ionized air and/or a chemical sterilization means, in particular hydrogen peroxide, is routed through the internal duct into the preform and/or routed out of the preform. Alternatively or additionally, it is advantageous in the use of UV emitters that the preforms are purged with nitrogen by way of the internal duct, so as to remove oxygen form the preforms, since otherwise ozone would be formed in the case of radiation using wavelengths of less than approx. 200 nm.

There are various possibilities for disposing the radiation source. In this way, a radiation source may be disposed so as to be fixed in height in relation to the blowing station, for example, and the stretching rod and/or the blowing nozzle during the height-positioning movement thereof are moved past the radiation source. This has the advantage that no relative movement of the radiation source in relation to the blowing station is necessary and complications in terms of construction caused thereby are avoided, on the one hand. On the other hand, a larger area than would be the case in a locationally fixed arrangement of the radiation source in relation to the stretching rod or to the blowing nozzle is covered with radiation.

Advantageously, the radiation source here is disposed so as to be positionally fixed in the blowing station, for example on a frame which supports the blow mold. This in comparison with an arrangement on moving parts, which is however also possible in principle, has advantages in terms of construction.

Here, the arrangement and the alignment are to be chosen such that the radiation source emits onto the stretching rod, onto that side of the blowing nozzle that faces the preform and optionally comes to bear on the preform, and/or onto the mouth region of the preform.

In the case of a plurality of blowing stations being disposed on a rotating blowing wheel, it is advantageous that each blowing station has a conjointly rotating sterilization installation. Advantages are to be seen both in terms of construction as well as in the impact of the sterilizing radiation (longer impact duration and shorter distance from the radiation source). A less preferable alternative would be, for example, that stationary radiation sources are disposed, the blowing stations rotating past said stationary radiation sources.

A preferred arrangement possibility lies in that a radiation source is disposed on the blowing nozzle and emits radiation onto the stretching rod and/or onto the mouth area of the preform and/or onto that blowing nozzle area that comes into contact with the preform. On account thereof, the radiation source sits very close to that area in which the radiation is to deploy its sterilizing effect. A further advantage is to be seen in that aligning the radiation source in this arrangement on the blowing nozzle is simple.

It furthermore advantageously proposed that the radiation source is configured so as to be centrically symmetrical, in particular so as to be annular, surrounds the area to be sterilized in an annular manner, and the sterilizing radiation is emitted into the annular interior. For example, this is also meant to refer to an arrangement in which the radiation source is composed of a plurality of sources, for example of three or more radiation sources which are disposed on a radius, the stretching rod or the blowing nozzle, for example, sitting in the center point thereof. On account thereof, the blowing nozzle, the stretching rod and/or the preform may be irradiated from all sides and in a comprehensive manner, without circumferential areas being omitted. To this end, the radiation sources are advantageously disposed distributed in an annular and equidistant manner on the circumference. A radiation source with is of annular configuration likewise achieves these advantages.

It is furthermore advantageously proposed that sterile air for configuring a sterile air curtain which surrounds the preform is blown down, in particular so as to flow in a laminar manner, around the blowing nozzle, in particular along the blowing nozzle and/or proceeding from the blowing nozzle and in the direction of the preform. The risk of renewed germ infestation may be further and effectively reduced by this sterile air curtain which is configured about the preform, since germs cannot penetrate the preform or be deposited thereon.

The advantages which have been described above for the method according to the invention apply in an analogous manner to the devices according to the invention.

Exemplary embodiments of the invention are illustrated in a schematic manner in the drawings, in which:

BRIEF DESCRIPTION OF THE DRAWING

FIG. 4 shows a modified heating section having an increased heating capacity;

FIG. 5 shows a schematic illustration of a preform having a stretching rod extended thereinto, according to a first and a second exemplary embodiment;

FIG. 6 shows a schematic illustration of a preform received in a blow mold, having a retracted stretching rod and a blowing nozzle which is disposed for impingement with blowing air;

DETAILED DESCRIPTION OF THE INVENTION

Figure 1:
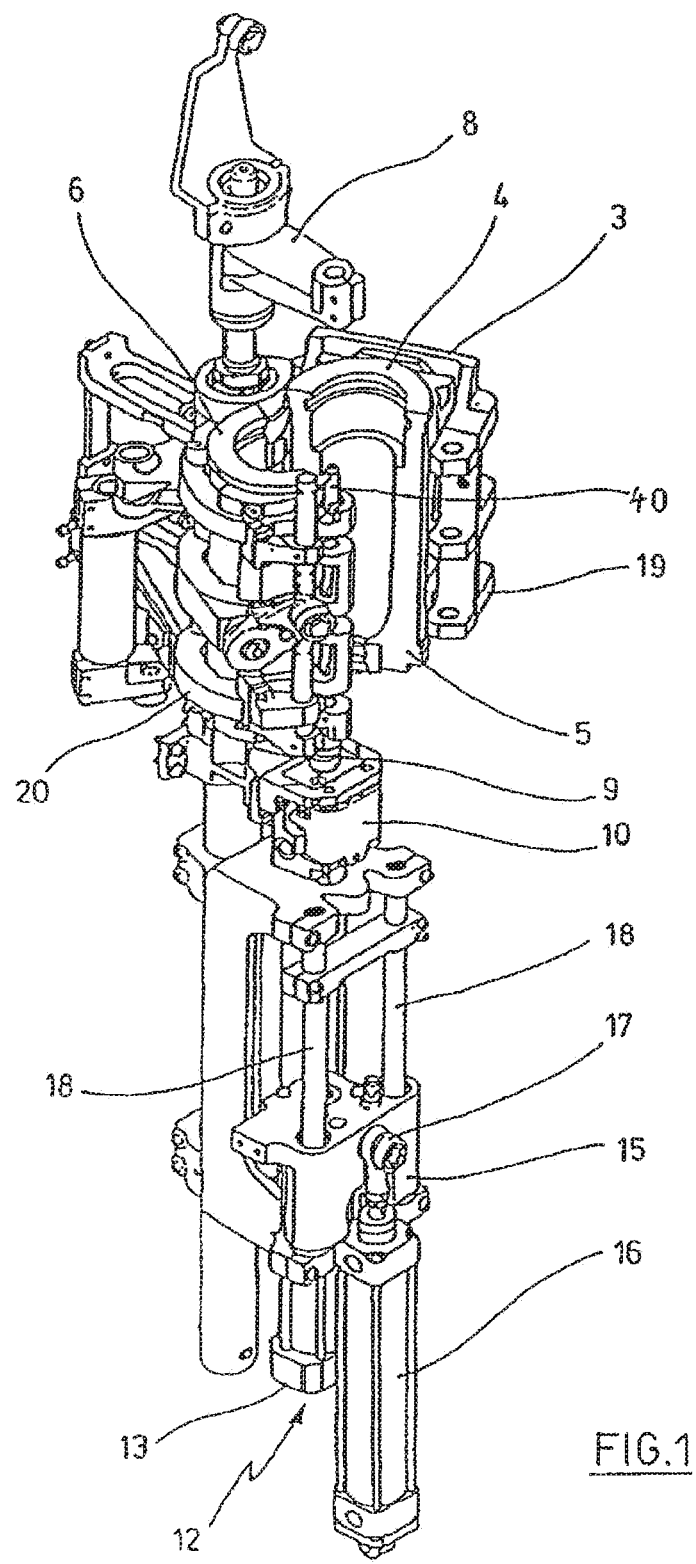
FIG. 1 shows a perspective illustration of a blowing station for manufacturing containers from preforms.
Figure 2:
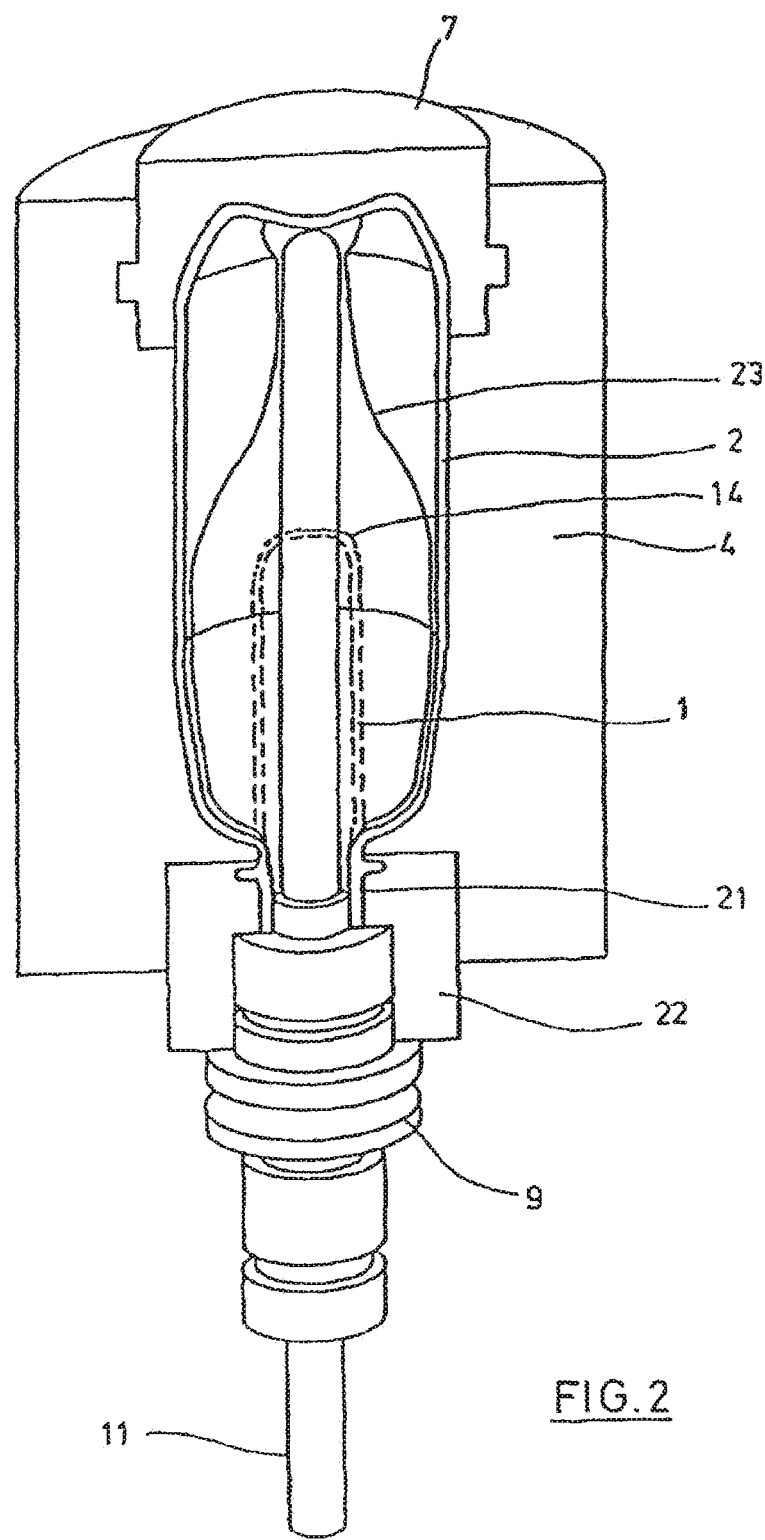
FIG. 2 shows a longitudinal section through a blow mold in which a preform is stretched and expanded.

The in-principle construction of a device for forming preforms 1 into containers 2 is illustrated in FIGS. 1 and 2.

The device for molding the container 2 is substantially composed of a blowing station 3 which is provided with a blow mold 4 into which a preform 1 is insertable. The preform 1 may be an injection-molded part made from polyethylene terephthalate. In order to enable insertion of the preform 1 into the blow mold 4, and in order to enable removal of the finished container 2, the blow mold 4 is composed of two mold halves 5, 6, and of a base part 7 which is positionable by a lifting device 8. The preform 1 in the area of the blowing station 3 may be held by a conveying mandrel 9 which together with the preform 1 passes through a plurality of treatment stations within the device. However, it is also possible for the preform 1 to be inserted directly into the blow mold 4 by way of tongs or other handling means, for example.

In order for a compressed-air supply line to be enabled, a blowing nozzle 10 which supplies compressed air to the preform 1 and at the same time performs sealing toward the conveying mandrel 9 is disposed below the conveying mandrel 9. However, in the case of a modified construction it is also conceivable that fixed compressed-air supply lines are used.

Stretching of the preform 1 is performed with the aid of a stretching rod 11 which is positioned by a cylinder 12. However, in-principle it is also conceivable for mechanical positioning of the stretching rod 11 to be carried out by curved segments which are impinged by tapping rollers. The use of curved segments is expedient in particular when a plurality of blowing stations 3 are disposed on a rotating blowing wheel. Use of cylinders 12 is expedient when blowing stations 3 which are disposed in a locationally fixed manner are provided.

In the embodiment illustrated in FIG. 1 the stretching system is configured in such a manner that a tandem arrangement of two cylinders 12 is provided. Prior to commencement of the stretching procedure per se, the stretching rod 11 is initially moved by a primary cylinder 13 into the area of a base 14 of the preform 1. During the stretching procedure per se the primary cylinder 13 having the extended stretching rod, together with a slider 15 which supports the primary cylinder 13, is positioned by a secondary cylinder 16 or by way of a cam control unit. In particular, it is contemplated that the secondary cylinder 16 is employed in a cam-controlled manner such that a current stretching position is predefined by a guide roller 17 which slides along a curved track while the stretching procedure is carried out. The guide roller 17 is pressed against the guide track by the secondary cylinder 16. The slider 15 slides along two guide elements 18. After the mold halves 5, 6 which are disposed in the area of supports 19, 20 have been closed, mutual interlocking of the supports 19, 20 with the aid of an interlocking installation 40 is performed.

In order for a mouth portion 21 of the preform 1 to be adapted to various shapes, the use of separate threaded inserts 22 is provided according to FIG. 2 in the area of the blow mold 4.

In addition to the blown container 2, FIG. 2 also shows the preform 1 having dashed lines and in a schematic manner a container bubble 23 under formation.

Figure 3:
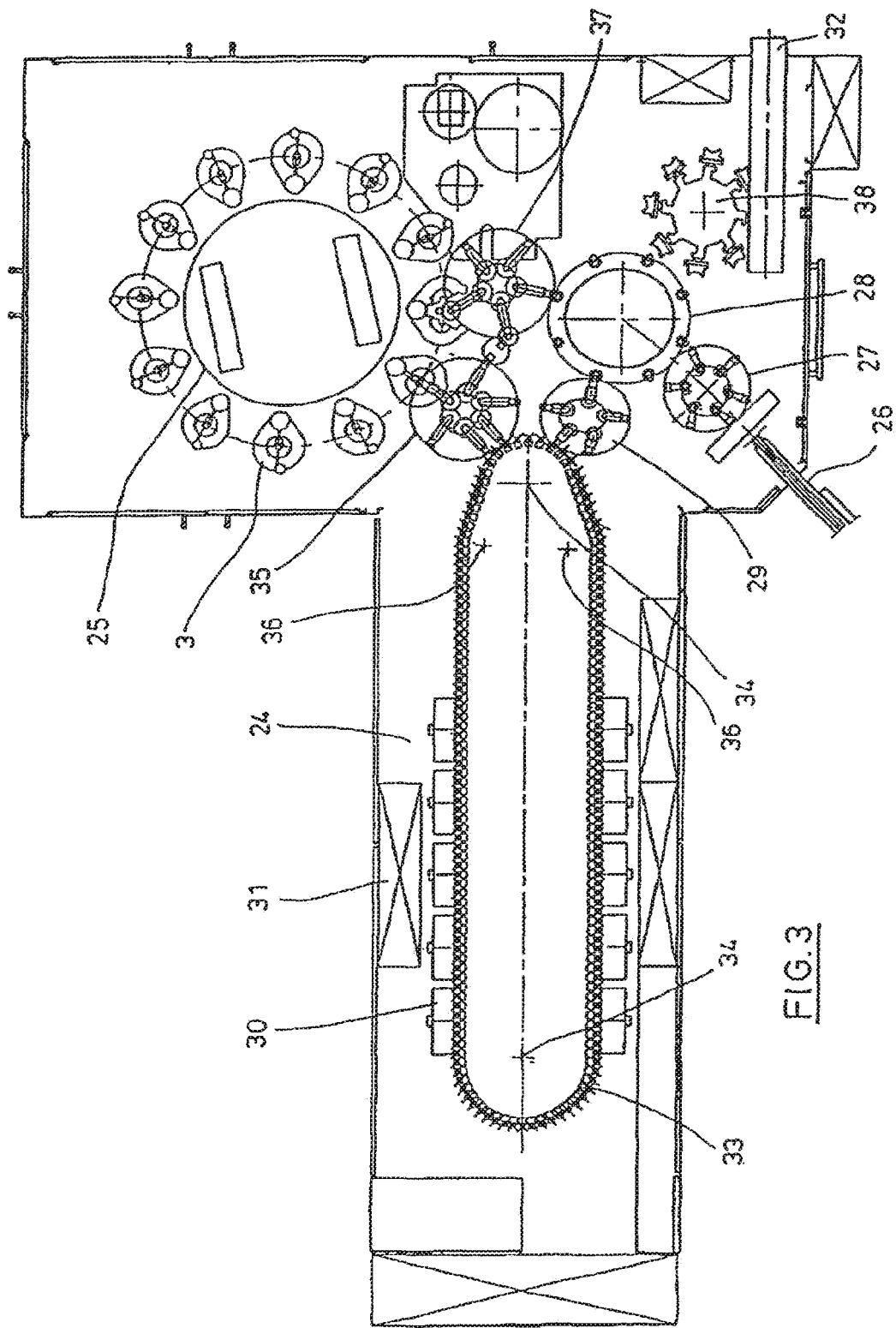
FIG. 3 shows a diagram to visualize an in-principle construction of a device for blow-molding containers.

FIG. 3 shows the in-principle construction of a blowing machine which is provided with a heating section 24 as well as a rotating blowing wheel 25. Proceeding from a preform infeed 26, the preforms 1 are conveyed into the area of the heating section 24 by transfer wheels 27, 28, 29. Heating radiators 30 and blowers 31 are disposed along the heating section 24, so as to temperature control the preforms 1. After sufficient temperature control of the preforms 1, the latter are transferred to the blowing wheel 25, the blowing stations 3 being disposed in the area thereof. The blown finished containers 2 are supplied to a delivery section 32 by further transfer wheels.

In order to be able to form a preform 1 into a container 2 in such a manner that the container 2 has material properties which guarantee a prolonged shelf life of foodstuffs, in particular beverages, which are filled into the container 2, special method steps must be adhered to when heating and orienting the preforms 1. Moreover, advantageous effects may be achieved by adhering to special dimensioning rules.

Various plastics may be used as the thermoplastic material. PET, PEN, or PP are employable, for example.

Expanding the preform 1 during the orientation procedure is performed by supplying compressed air. The compressed-air supply is subdivided into a pre-blowing phase in which gas, for example compressed air, is supplied at a low pressure level, and into a subsequent main blowing phase in which gas is supplied at a comparatively high pressure level. During the pre-blowing phase, compressed air at a pressure in the range of 10 bar to 25 bar is typically used, and during the main blowing phase, compressed air at a pressure in the range of 25 bar to 40 bar is supplied.

It can likewise be seen in FIG. 3 that the heating section 24 in the embodiment illustrated is configured from a plurality of revolving conveying elements 33 which are strung together in a chain-like fashion and are guided along by deflection wheels 34. In particular, it is contemplated that a substantially rectangular basic contour is defined by the chain-like arrangement. In the case of the embodiment illustrated, a single deflection wheel 34 which is of comparatively large size is used in the area of that extent of the heating section 24 that faces the transfer wheel 29 and an infeed wheel 35, and two deflection wheels 36 which are of comparatively small size are used in the area of adjacent deflections. However, other guides are also conceivable in principle.

In order for as tight a mutual arrangement of the transfer wheel 29 and of the infeed wheel 35 as possible to be enabled, the arrangement illustrated has proven particularly expedient, since three deflection wheels 34, 36, are positioned in the area of the respective extent of the heating section 24, and specifically in each case the comparatively small deflection wheels 36 in the area of the transition toward the linear profiles of the heating section 24, and the comparatively large deflection wheel 34 in the immediate transfer area to the transfer wheel 29 and to the infeed wheel 35. As an alternative to the use of chain-like conveying elements 33, it is also possible for a rotating heating wheel to be used, for example.

After blowing of the containers 2 has been completed, the latter are guided out of the area of the blowing stations 3 by a retrieval wheel 37 and by way of the transfer wheel 28 and a delivery wheel 38 are conveyed to the delivery section 32.

On account of the higher number of heating radiators 30, a larger amount of preforms 1 per unit of time may be temperature controlled in the modified heating section 24 illustrated in FIG. 4. The blowers 31 here direct cooling air into the area of cooling air ducts 39 which in each case lie opposite the assigned heating radiators 30 and discharge the cooling air via outflow openings. On account of the arrangement of the outflow directions, a streaming direction for the cooling air that is substantially transverse to a conveying direction of the preforms 1 is implemented. The cooling air ducts 39 in the area of those surfaces that lie opposite the heating radiators 30 may provide reflectors for the radiation of heat; it is likewise possible for cooling of the heating radiators 30 to be implemented by way of the dissipated cooling air.

In a schematic and very simplified manner, FIG. 5 shows two exemplary embodiments for the configuration of a sterilization installation in a blowing station. In order for the illustration to be simplified, only the preform 1 is shown. It is not shown, in particular, that this preform 1 is received in a blow mold. Further parts of the blowing station which are not relevant to the explanation of this exemplary embodiment have likewise been omitted for the sake of simplification.

The right half of FIG. 5 shows a stretching rod 11 which in a known fashion is manufactured from a metallic material, for example. In order for the preform 1 to be stretched, the stretching rod 11 is positioned in terms of height. To this end, a lifting device (not illustrated) such as has been explained in the context of FIG. 1, for example, is provided. A plurality of UV emitters 51 which emit UV radiation 52 in the direction of the stretching rod 11 are disposed in a height-specific area of the stretching rod 11. On account of this UV radiation 52, the stretching rod 11 in the irradiated area is de-germed or kept germ-free, respectively. In the stretching procedure or during height-specific positioning of the stretching rod 11, respectively, the stretching rod 11 travels through the UV emitters 51 which are disposed on opposite sides and, on account thereof, a new area of the stretching rod 11 is continuously irradiated by UV radiation 52. Height-specific positioning of the UV emitters 51 here is preferably chosen such that the stretching rod 11, commencing with the stretching rod tip 53, in the course of the height-related movement thereof is swept with UV radiation 52. In this way, that entire area of the stretching rod 11 that during the stretching process is driven into the preform 1 is reliably impinged with UV radiation 52. The UV emitter 51 may be configured so as to be annular, for example. However, a plurality of UV emitters 51 which surround the stretching rod 11 in an annular manner may also be provided. The state illustrated corresponds approximately to the point in time at which the stretching rod tip 53 comes to bear on the preform base 14 and begins to exert a stretching force.

The left half of FIG. 5 shows an embodiment of the invention which in relation to the right half is modified. In this left half, the stretching rod 11 is manufactured from a material which conducts UV radiation. The configuration from a quartz glass is contemplated here in particular. As has also been set forth with reference to the right half of FIG. 5, UV emitters 51 which emit UV radiation 52 in the direction of the stretching rod 11 are disposed in a height-specific area of the stretching rod 11. On account of the configuration of the stretching rod being of a quartz glass, for example, the UV radiation 52 may enter into the stretching rod 11. The UV radiation 52 is routed within the stretching rod 11, in particular in the direction of the preform 1, and via the stretching-rod surface and via a height-specific area h of the stretching rod 11 exits from the latter and in particular impacts the internal surface 54 of the preform 1.

Routing the UV radiation 52 within the stretching rod 11 may be supported in that launching means (not illustrated) are provided, so as to launch the UV radiation 52 into the stretching rod 11 in a targeted manner. For example, a reflecting mirror, a prism, or similar, could be disposed in a launching area. The UV radiation 52 could also be infed into the stretching rod 11 from the outside by means of UV-conducting optical fibers, for example. Means which facilitate the emission of UV radiation may also be provided in the stretching rod 11 or on the stretching rod. For example, diffuser bodies may be provided along a length area h of the stretching rod 11 in the material of the stretching rod, or the surface of the stretching rod 11 by way of a facet cut may be configured for targeted emission. Preferably, the stretching rod 11 emits UV radiation 52 along a length area h which, commencing at the stretching rod tip 53, runs up to a height which corresponds to the height up to which the stretching rod 11 is immersed when being driven into the preform 1 up to contact with the base area 14 of the preform 1. However, the emission area may also be longer, so as to release UV radiation 52 during the stretching process as far as possible along the entire height-specific area of the container 2 under development, for example.

As a further modification in relation to the right half of FIG. 5, the stretching rod 11 in the left half of FIG. 5 has a central bore 55 through which ionized air 56 may be blown into the preform 1, so as to blow out contaminations from the preform 1, for example. By way of this internal duct 55, hydrogen peroxide 57 or another suitable chemical sterilizing means, for example in the gaseous aggregate state, may be introduced into the preform 1, so as to bring about additional sterilizing. It is also conceivable for this internal duct 55 to be used not for infeeding the mentioned media but for discharging, that is to say that the ionized air 56 or the gaseous hydrogen peroxide 57, respectively, could be discharged from the preform 1 by way of this internal duct 55. In a fashion not illustrated, the stretching rod 11 may also have a plurality of internal ducts 55 which then are usable both for the supply and for the discharge of the media, for example. It is also possible for ionized air 56 to be supplied or discharged, respectively, by way of one of the ducts 55 and for hydrogen peroxide 57 to be supplied and discharged, respectively, by way of another of the ducts 55. It is also conceivable for all ducts 55 to the used in the same way for the supply and/or for the discharge of the mentioned media. These variants may all also be transferred to the stretching rod 11 of the right half of the picture.

FIG. 6 in a very schematic illustration shows a further exemplary embodiment of the invention. A blowing nozzle 10 which serves for supplying blowing air, as has already been explained by means of FIG. 1, for example, is shown. It is provided according to the invention that UV emitters 60 are disposed within the blowing nozzle 10. These UV emitters 60 here are disposed such that the emission of the UV radiation 61 is performed in the direction of the stretching rod 11. At the same time, the neck area 21 of the preform 1 is irradiated, and the interior 62 of the blowing nozzle 10 is also impinged with UV radiation 61. Here too, the UV emitters 60 may be disposed in an annular manner or be configured in an annular manner. On account of the relative movement between the blowing nozzle 10 and the stretching rod 11, a specific length area of the stretching rod 11 is illuminated by UV radiation 61, said specific length area commencing at the stretching rod tip 53 and running up to a terminal position of the stretching rod 11. Additionally, further UV emitters 51 which emit UV radiation 52 in the direction of the stretching rod 11 are disposed outside and above the blowing nozzle 10. To this end, reference may be made to FIG. 5.

Figure 7:
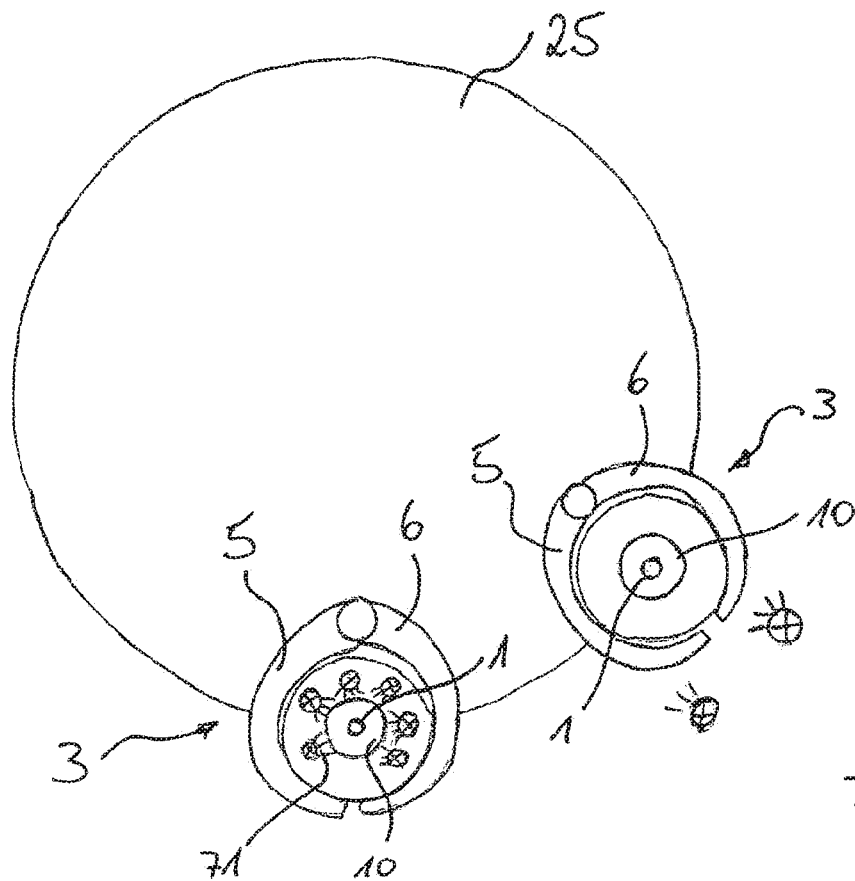
FIG. 7 shows in a schematic illustration two blowing stations, shown in an exemplary manner, on a rotating blowing wheel having a sterilizing installation, according to a first and a second exemplary embodiment.

FIG. 7 in a very schematic illustration shows a blowing wheel 25 having two blowing stations 3 which are illustrated in an exemplary manner and have in each case two blow mold halves 5, 6. The blowing station 3 which is shown at the 6 o'clock position of the blowing wheel 25 has UV emitters 70 which surround the blowing nozzle 10 in an annular manner. These emitters 70 are disposed and aligned such that the blowing nozzle 10 is impinged with UV radiation 71. Preferably, the UV emitters 70 are aligned such that the lower area of the blowing nozzle 10, which faces the preform 1, is irradiated, in particular that area that comes into contact with the preform 1. As soon as the blowing nozzle 10 commences the lowering movement thereof in order to be lowered in a sealing manner onto the preform 1, the adjacent area of the blowing nozzle 10 is also irradiated with UV radiation 71.

The blowing station 3 which is shown in the 4 o'clock position of the blowing wheel 25 has UV emitters 73 which are disposed in a stationary manner and in terms of height are positioned and aligned such that the blowing nozzle 10 which is being moved past is irradiated with UV radiation 74. Here too, irradiation of that side of the blowing nozzle 10 that faces the preform 1 is preferably performed.

Figure 8:
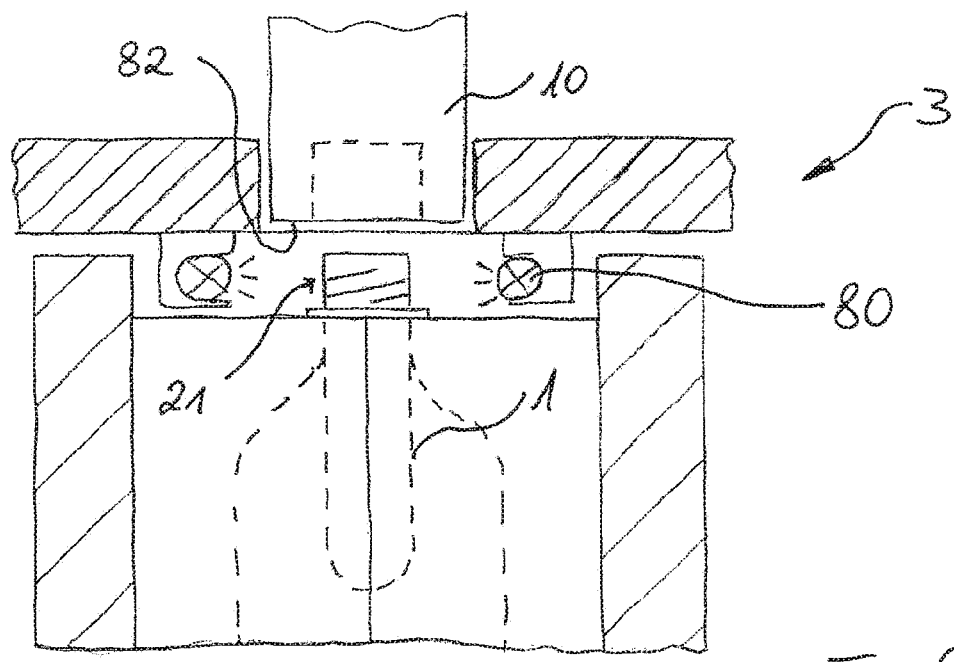
FIG. 8 shows in a schematic sectional illustration an arrangement of the sterilizing installation within a blowing station.

FIG. 8 in a schematic sectional illustration shows the arrangement of UV emitters 80 on a fixed part of the blowing station 3. It can be seen that the UV radiation 81 not only impinges the lower side 82 of the blowing nozzle 10 but also the neck area 21 of the preform 1. As soon as the stretching rod (not illustrated) is positioned through the blowing nozzle 10 in the direction of the preform 1, the stretching rod 11 is also irradiated with UV light. All areas which are relevant to reliable sterilizing or sterile keeping are covered with sterilizing radiation in the fashion narrated.

The invention claimed is:

1. A device for manufacturing blow-molded containers which are sterile in at least some areas, that device comprising: a heating section for temperature controlling preforms of a thermoplastic material; at least one blowing station for blow-molding the preforms to form containers, wherein a blowing station of the at least one blowing station has a stretching rod for stretching a preform of the preforms and a blowing nozzle for impinging the preform with a pressurized fluid; and a sterilization installation disposed in the blowing station, wherein the sterilization installation has at least one radiation source that emits a sterilizing radiation onto the stretching rod and/or onto the blowing nozzle, wherein the at least one radiation source is arranged outside of a blow mold and is disposed so as to be positionally fixed in relation to the blowing station such that the at least one radiation source emits radiation onto a side of the blowing nozzle that faces the preform and/or onto a mouth area of the preform.

2. The device as claimed in claim 1, wherein the sterilization installation is actuatable to emit sterilizing radiation during blow-molding and/or during an inline operation and/or during start-up of the device.

3. The device as claimed in claim 1, wherein the at least one radiation source is configured as a UV radiation emitting UV radiation source.

4. The device as claimed in claim 3, wherein the stretching rod is made of a UV radiation conducting material.

5. The device as claimed in claim 4, wherein the stretching rod is made of a quartz glass.

6. The device as claimed in claim 1, wherein the stretching rod has at least one internal duct that is connected in a valve-controlled manner to a source or sink for ionized air and/or to a source or sink for a chemical sterilization agent, so as to route ionized air and/or the chemical sterilization agent through the at least one internal duct into the preform and/or out of the preform.

7. The device as claimed in claim 1, wherein the at least one radiation source is disposed so as to be fixed in height in relation to the blowing station in so that the stretching rod and/or the blowing nozzle during a height-positioning movement thereof are moved past the at least one radiation source.

8. The device as claimed in claim 7, wherein the at least one blowing station comprised of a plurality of blowing stations which are disposed on a rotating blowing wheel and each blowing station of the plurality of blowing stations has a conjointly rotating sterilization installation.

9. The device as claimed in claim 1, wherein the at least one radiation source is disposed on the blowing nozzle such that the at least one radiation source emits radiation onto the stretching rod and/or onto the mouth area of the preform and/or onto a blowing nozzle area that comes into contact with the preform.

10. The device as claimed in claim 1, wherein the at least one radiation source is configured so as to be centrically symmetrical which surrounds an area to be sterilized in an annular manner, and emits the sterilizing radiation into an annular interior.

11. The device as claimed in claim 1, further comprising sterile air outlets in an area of the blowing station, the sterile air outlets being supplied with sterile air and being disposed and configured so that sterile air for configuring a sterile air curtain is blown down around the blowing nozzle.

12. The device as claimed in claim 11, wherein the sterile air outlets are disposed and configured to blow down the sterile air curtain in a laminar flow along the blowing nozzle or proceeding from the blowing nozzle in a direction of the preform.

\* \* \* \* \*